United States Patent [19]

Prezelj et al.

[11] 4,334,964
[45] Jun. 15, 1982

[54] PROCESS FOR SEPARATING THE REACTION PRODUCTS OBTAINED FROM ETHERIFYING LOWER ISOOLEFINS WITH METHANOL

[75] Inventors: Milan Prezelj, Frankfurt am Main; Günter Osterburg, Duisburg; Joachim E. Putz, Dreieich-Offenthal, all of Fed. Rep. of Germany

[73] Assignee: Edeleanu Gesellschaft mbH, Frankfurt am Main, Fed. Rep. of Germany

[21] Appl. No.: 273,171

[22] Filed: Jun. 12, 1981

[30] Foreign Application Priority Data

Jun. 27, 1980 [DE] Fed. Rep. of Germany ....... 3024147

[51] Int. Cl.$^3$ ............................................. B01D 3/34
[52] U.S. Cl. ........................................ 203/14; 203/84; 203/85; 203/97; 203/98; 203/DIG. 19; 568/699
[58] Field of Search ....................... 203/12, 14, 28, 29, 203/31, 32, 38, 75, 78, 82, 84, 95, 97, DIG. 6, DIG. 19, 76, 79, 83, 85, 39; 568/699, 688, 689; 44/53, 54, 56, 77

[56] References Cited

U.S. PATENT DOCUMENTS

| 3,846,088 | 11/1974 | Brown et al. | 568/699 |
| 4,144,138 | 3/1979 | Rao et al. | 203/DIG. 19 |

FOREIGN PATENT DOCUMENTS 2547380 8/1976 Fed. Rep. of Germany .
2706465 2/1977 Fed. Rep. of Germany .

*Primary Examiner*—Frank Sever
*Attorney, Agent, or Firm*—Carl G. Ries; Robert A. Kulason; James J. O'Loughlin

[57] ABSTRACT

A method for separating a mixture of reaction products produced in the catalytic etherification of a lower isoolefin with methanol wherein said reaction product comprises a mixture of ether, methanol, unreacted hydrocarbon and tertiary alcohol which comprises adding water to said reaction product to form a hydrocarbon phase containing said ether and an aqueous phase containing methanol and a tertiary alcohol, separating said hydrocarbon phase to recover a methyltertiary alkyl ether, introducing said alcohol-containing aqueous phase into a distillation column to separate a methanol fraction overhead, withdrawing a side stream rich in tertiary alcohol from said distillation column, stripping this side stream in a stripping column to separate a second methanol fraction overhead and a tertiary alcohol bottoms fraction and recycling the methanol overhead fraction from the stripping column to the upper part of the distillation column and recycling the overhead methanol fraction from the distillation column to the feed stream to said reactor.

11 Claims, 2 Drawing Figures

PROCESS FOR SEPARATING THE REACTION PRODUCTS OBTAINED FROM ETHERIFYING LOWER ISOOLEFINS WITH METHANOL

BACKGROUND OF THE INVENTION

1. Field of the Invention

It known to manufacture ethers by reacting an olefin with methanol in the presence of an acid catalyst. Thus, methyl tertiary butyl ether (MTBE) and methyl tertiary amyl ether (TAME) may be prepared by reacting isobutene and isopentene respectively with methanol in the presence of an acidic cation exchange resin catalyst. This reaction leads to the formation of a reaction product mixture comprising the desired ether together with unreacted methanol, unreacted hydrocarbons and some tertiary alcohol by-product.

It is conventional to add water to this reaction product to effect a phase separation, namely a separation of the ether in an organic hydrocarbon phase and a separation of the alcohols in an aqueous phase. These two phases are generally treated separately in distillation columns in order to effect the separation and recovery of the ether product and to effect the separation of the methanol for recycle to the feed stream which is necessary in order to provide an efficient process.

The tertiary alcohol by-product produced in the reaction is extracted with the methanol into the aqueous phase in the phase separation step. When this aqueous phase is distilled to effect the separation of the methanol for recycle, a tertiary alcohol-water azeotrope is distilled with the methanol and recycled with the methanol to the reactor. This leads to a build-up of water in the feed stream to the reactor with certain deleterious effects on the overall efficiency of the process. In particular, the presence of water in the isoolefin-methanol feed stream to the reactor causes a shift in the course of the reaction leading to the formation of excessive amounts of tertiary alcohol and a suppression or reduction in the yield of the desired ether product from the reaction.

An object of this invention is to provide an improved process for the production and separation of methyltertiary alkyl ethers.

Another object of this invention is to provide a more efficient process including the high conversion of the reactants and utilization of by-products from the reaction.

Another object of this invention is to provide valuable blending agents for motor fuel compositions.

2. Description of the Prior Art

DE-OS No. 2,547,380 discloses a process for the preparation of ethers and the separation of the ether-containing reaction mixture by means of a washing step immediately downstream from the reactor. The sequence of processing steps disclosed in the washing prior to separation by distillation has the advantage that there is no limitation with respect to the amount of methanol present and the complete removal of the alcohol is effected in a single process step without resort to a series of azeotropic distillations.

DE-AS 2,706,465 discloses a two-step process for methyl tertiary butyl ether production.

SUMMARY OF THE INVENTION

The novel process of the invention provides a method for separating a mixture of reaction products produced in the catalytic etherification reaction of a lower isoolefin having from 4 to 7 carbon atoms with methanol wherein said reaction product comprises a mixture of ether, methanol, unreacted hydrocarbon and a tertiary alcohol which comprises adding water to said reaction mixture to form a hydrocarbon phase containing said ether and an aqueous phase containing methanol and a tertiary alcohol, separating said hydrocarbon phase to recover a methyl tertiary alkyl ether, introducing said alcohol-containing aqueous phase into a distillation column to separate a methanol fraction overhead, withdrawing a side stream rich in tertiary alcohol from said distillation column, stripping this side stream in a stripping column to separate a second methanol fraction overhead and a tertiary alcohol bottoms fraction and recycling said methanol overhead fraction from the stripping column to the upper part of the distillation column and recycling the overhead methanol fraction from the distillation column to the feed stream to said reactor.

DETAILED DESCRIPTION OF THE INVENTION

In accordance with this invention, a reaction product mixture, resulting from the etherification reaction of methanol and an isoolefin feed stream comprising hydrocarbons having from 4 to 7 carbon atoms in a catalytic reactor, which comprises a mixture of methyl tertiary alkyl ether, unreacted hydrocarbon, unreacted methanol and a tertiary alcohol, is contacted with water to effect a phase separation of the methyl tertiary alkyl ether in an organic hydrocarbon phase and methanol and by-product tertiary alcohol in an aqueous phase, separating said hydrocarbon phase in a separating column to recover methyl tertiary alkyl ether, separating said aqueous phase by introducing it into a distillation zone effective for the distillation of a methanol fraction overhead, withdrawing a side stream rich in tertiary alcohol from said distillation zone and introducing this side stream into a stripper, stripping this side stream in said stripper to recover a second methanol fraction overhead and a bottoms fraction comprising aqueous tertiary alcohol, and recycling said methanol overhead fraction from the stripper to the upper part of the distillation column and recycling the overhead methanol fraction from the distillation column to the feed stream to said reactor. Optionally, said bottom fraction containing aqueous tertiary alcohol (about 80% by weight tertiary alcohol, and 20% by weight water) is added to the feed stream of the hydrocarbon separation column and the recovered methyl tertiary alkyl ether fraction and tertiary alcohol are used for blending in a fuel composition, such as gasoline.

The isoolefins employed in this process are those having from 4 to 7 carbon atoms. The preferred isoolefins for the reaction are isobutylene and isoamylene. Straight chain olefins are essentially non-reactive in this process.

The reaction product from the reaction comprises a mixture of the methyl tertiary alkyl ether product in combination with unreacted hydrocarbon, unreacted methanol and tertiary alcohol as more fully described hereinbelow. This mixture is contacted with water to effect a phase separation between the organic hydrocarbon soluble ethers and the water extracted alcohols. In a typical example, the aqueous phase or aqueous extract will comprise from about 5 to 10 weight percent methanol, from about 0.5 to 1 weight percent of methyl tertiary alkyl ether and from about 0.3 to 0.5 weight percent of tertiary alkanol.

The aqueous phase is introduced into a distillation zone or distillation tower to separate the alcohol from the water. Desirably, the ratio of methanol to water should range from about 1 part alcohol to from about 10 to 20 parts of water. In this distillation, a fraction rich in tertiary alcohol will be produced in an intermediate zone in the distillation column. In accordance with this process, a side stream rich in said tertiary alcohol is removed from the distillation column and directed to a stripper. This stripper is a relatively small stripping column having approximately one tenth throughput capacity of the distillation tower. In a typical process in which isobutylene was reacted with methanol to produce methyl tertiary butyl ether and by-product tertiary butyl alcohol, the side stream consisted of about 40 percent tertiary butyl alcohol (TBA), 50 percent methanol and 10 percent water. In general, the side stream rich in tertiary alcohol should be taken at an intermediate point in the distillation column where the side stream comprises from about 30 to 50 percent of tertiary alcohol and preferably from about 40 to 45 percent tertiary alcohol.

This side stream is subjected to stripping in the stripper to effect the separation of methanol overhead and the recovery of a bottoms fraction comprising tertiary alkanol. The overhead fraction from the stripper is recycled to the upper part of the distillation column and the methanol fraction from the distillation column is recycled back to the feed stream to the reactor.

The organic phase is separated by distillation in a separate distillation zone with the recovery of methyl tertiary alkyl ether in the bottoms fraction from this separation.

This process leads to a greater than 99.5% utilization of the methanol feed as well as to the utilization of the tertiary alcohol by-product produced in the reaction.

Figure 1:
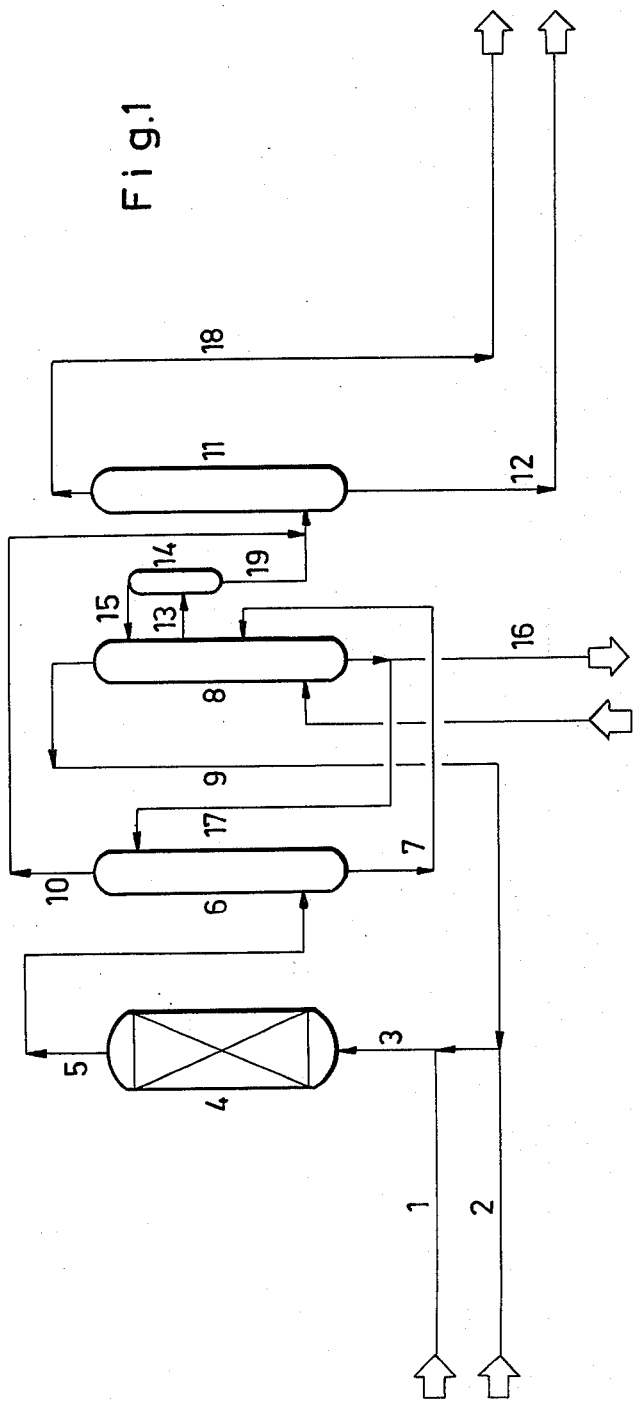
FIG. 1 illustrates the practice of this invention in its single-step mode.
Figure 2:
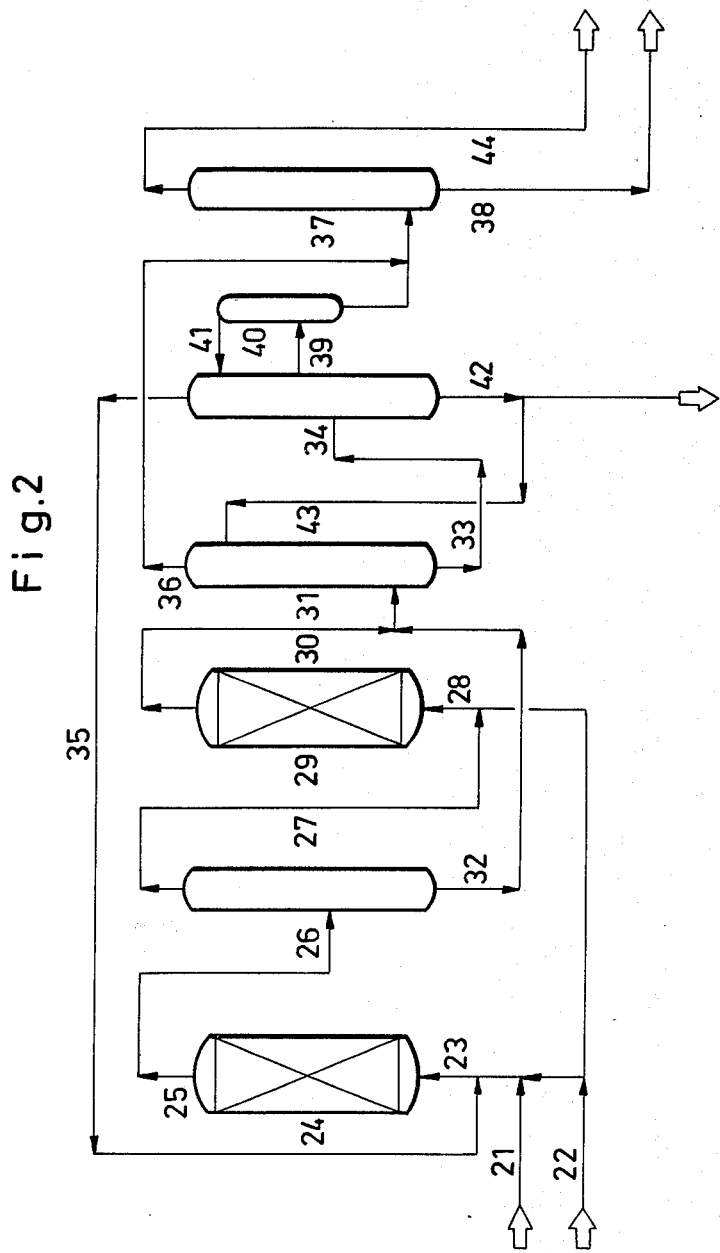
FIG. 2 illustrates the practice of this invention in a two-step mode.

An isobutene containing $C_4$-hydrocarbon stream from line 1 and methanol from line 2 flow through line 3 to the reactor 4. The reaction mixture leaves the reactor 4 through line 5 and is introduced into the lower portion of the wash column 6, in which the alcohol components are extracted with water. In the bottom portion of the wash column 6 an aqueous mixture is collected which in addition to water contains about 5 to 10% by weight of methanol, 0.5 to 1% by weight of MTBE and 0.3 to 0.5% by weight of TBA. Through line 7 this mixture is supplied to the distillation column 8, where the methanol is driven off overhead and is supplied through line 9 to the line 3 associated with the reactor 4 to participate again in the reaction. MTBE together with the non-reacted $C_4$-hydrocarbons leaves the wash column 6 through line 10 and passes therethrough into distillation column 11, where the pure MTBE is separated in the bottom portion and is discharged through line 12. At the tray of the distillation column 8 having a high TBA concentration, a few trays above the entry of line 7 into the column, a TBA-containing side stream is fed through line 13 to the small stripping column 14 which is only about one tenth the size of the main column 8.

The volume of this side stream is rated such that a control device (not shown) at the top of column 8 no longer indicates any TBA. Based on the amount of methanol contained in the side stream, the latter comprises about 10 to 20% by weight of the methanol contained in the aqueous extract. The typical composition of this stream is: about 40% by weight of TBA; about 50% by weight of MeOH, and about 10% by weight of $H_2O$. The column 14 is heated by a heating unit provided in the bottom portion. The aqueous TBA collects in the bottom of the column 14; the methanol as vapor leaves the top of the column 14 and is returned to the main column through line 15. The water collected in the bottom of column 8 is discharged through line 16 or, respectively, is in part transferred to the wash column 6 through line 17. The vapor mixture escaping from the top of the hydrocarbon-MTBE-separating column 11 only contains the non-reacted components of the $C_4$-hydrocarbon mixture and leaves the plant through line 18.

The methanol-free water containing TBA drawn from the bottom of column 14 may be added through line 19 to the stream passing through line 10, and is introduced therewith to the column 11. Here, it is collected together with the MTBE as a bottom product and is discharged together with the MTBE through line 12, while its water content escapes from the top of the column and is separated from the $C_4$-hydrocarbon mixture after condensation in a trap (not shown).

An isobutene containing $C_4$-hydrocarbon stream from line 21 and methanol from line 22 flow through line 23 to the reactor 24. The reaction mixture exits from the reactor 24 through line 25 and enters the distillation column 26. The overhead product, which is a $C_4$-hydrocarbon mixture with a residual content of non-reacted isobutene, is drawn off through line 27 and, together with fresh methanol from line 28, is introduced to the reactor 29, where the reaction of the residual isobutene takes place. The reaction mixture of non-convertible $C_4$-hydrocarbons, ether, and alcohol escapes at the top of the reactor 29 through line 30 and enters the wash column 31 in the lower portion thereof after the bottom product of column 26 drawn off through line 32 has been added to line 30. In the wash column 31 the alcohol component is extracted with water. In the bottom of wash column 31 an aqueous mixture collects, which in addition to water contains about 5 to 10% by weight of methanol, about 0.5 to 1% by weight of MTBE, and about 0.3 to 0.5% by weight of TBA. Through line 33 this mixture is introduced to the distillation column 34, where the methanol escapes overhead and through line 35 is added to the line 23 associated with the reactor 24 so as to again participate in the reaction. MTBE together with the hydrocarbon components leaves the wash column 31 at the top through line 36 and flows therethrough to the distillation column 37, where the pure MTBE is separated in the bottom portion and discharged through line 38. On that tray of the distillation column 34 having a high TBA concentration, a few trays above the entry of line 33 into the column, a TBA-containing side stream is passed through line 39 into the small stripping column 40, which is only about one-tenth the size of the main column 34. The volume of this side stream is determined such that a control device (not shown) at the top of the column 34 does not indicate any TBA. Based on the amount of methanol contained in the side stream, the latter contains about 10 to 20% by weight of the methanol contained in the aqueous extract. The typical composition of the side stream is about 40% by weight of TBA; about 50% by weight of MeOH, and about 10% by weight of H₂O. This column 40 is heated by means of a heating unit provided in the bottom portion. The aqueous TBA collects in the bottom of column 40; the methanol as vapor leaves the top of the column 40 and is returned to the main column through line 41. The water collected in the bottom of the column 34 is discharged through line 42 and, respectively, is partially transferred through line 43 to the wash column 31.

The vapor mixture leaving the column 37 overhead only contains the non-convertible components of the $C_4$-hydrocarbon mixture and leaves the plant through line 44. The methanol-free water containing TBA drawn from the bottom of the column 40 may be added through line 45 to the stream in line 36 and together with the same is introduced to the column 37. Here it is collected together with the MTBE as a bottom product and is discharged therewith through line 38, while its water content escapes from the top of the column and is separated from the $C_4$-hydrocarbon mixture after condensation in a trap (not shown).

The following detailed example illustrates the practice of this invention.

6,527 parts of methanol from line 2, together with 1,679 parts of methanol from line 9, are passed to the reactor 4 where they react with 66488 parts hydrocarbon feed over a synthetic ion exchange resin catalyst, Amberlyst 15, which is a sulfonated styrene-divinylbenzene copolymer in the acid form.

TABLE I

| COMPOSITION OF THE HYDROCARBON STREAM | | |
|---|---|---|
| Component | Mole-% | Parts by Weight |
| Isobutene | 31.0 | 21077 |
| n-Butane | 10.1 | 6848 |
| Trans-butene-2 | 15.6 | 10239 |
| cisbutene | 11.2 | 7314 |
| 1-butene | 13.8 | 9042 |
| Isobutene | 18.3 | 11968 |
| Total | 100.0 | 66488 |

The reaction in the reactor takes place at 70° C. and 12 bars.

Isobutene and methanol react by forming a reaction mixture containing the desired methyl-t-butylether.

The conversion of isobutene is in the order of 96%. The 1-butene, the cis- and trans-butene 2, the isobutane and the n-butane pass through the reactor as inert hydrocarbons.

With water content of the feed stock caused by the slight amounts of water of 0.03% entrained in the methanol stream and the hydrocarbon stream, 0.6% of the supplied isobutene are converted to TBA.

The product stream drawn from the reactor 4 has the following composition:

TABLE II

| Component | Parts |
|---|---|
| methanol | 1,679 |
| TBA | 90 |
| isobutene | 478 |
| inert hydrocarbons | 54,520 |
| product ether | 17,949 |

In wash column 6 this product stream is washed with 16,000 parts of water (ratio: 90 parts of water, 10 parts of alcohol). The pressure in the wash column is 10 bars so that the hydrocarbons are maintained in the liquid phase. Methanol and TBA are completely extracted by the water and collect as extract in the bottom of the column. The extract contains 15,890 parts of water
1,679 parts of methanol
90 parts of TBA
125 part of MTBE.

The refined product comprises:

17,824 parts of MTBE
54,998 parts of inert hydrocarbons
110 parts of water and is separated in the fractionating tower 11 into inert hydrocarbons and MTBE:

54,998 parts of inert hydrocarbons
17,824 parts of MTBE.

In a separator (not shown) the water is separated from the condensate. The methanol is driven from the aqueous alcohol phase in the methanol-water separating column 8, which operates the stripping stream.

From the tray having the highest TBA concentration, viz., the 28th tray a side stream is drawn off and passed to a small side column 14. A control device at the head of the main column does not indicate any substantial amounts of TBA.

A side stream is drawn off consisting of
113 parts of methanol
90 parts of TBA
22 part of H₂O.

The 113 parts of methanol leave the side column 14 in vaporous form and are returned through line 15 to the main column 8, while 90 parts of TBA and 22 parts of H₂O collect in the bottom of the side column 14.

The amount of methanol in the stream leaving the top of the column corresponds to that washed out in column 6, i.e., 1,679 parts. The stream furthermore contains 125 parts of dissolved MTBE.

The foregoing results demonstrate a novel process for the efficient manufacture of ethers from isoolefins and methanol coupled with an efficient use of by-products from the reaction.

A reflux stream, which is not entered in the schematic diagram, keeps the water content of the methanol vapor exiting from the top of column 8 below 0.1%=below 1.7 parts.

After condensation the methanol is returned to the reactor without loss.

The bottom product in the side column 14, together with the overhead product of the wash column 6, is passed to the distillation column 11 where the hydrocarbons and the water contained in the bottom product are separated.

Composition of the overhead product:

hydrocarbons: 54,998 part
water: 130 parts.

After condensation, the water is separated in a water separator.

The bottom product consists of 17,823 parts of MTBE
90 parts of TBA 2 parts of H₂O

We claim:

1. In a method for the production of an ether from the reaction of methanol and an isoolefin hydrocarbon feed stream in which the hydrocarbons have from 4 to 7 carbon atoms in a catalytic reactor wherein water is added to the reaction product from said reaction resulting in the formation of an organic hydrocarbon phase comprising said ether and unreacted hydrocarbons and an aqueous phase comprising methanol and a tertiary alcohol, and wherein said organic hydrocarbon phase is separated into an ether fraction and said aqueous phase is distilled in a distillation column to separate a methanol fraction overhead from said aqueous phase, the improvement which comprises withdrawing a side stream rich in tertiary alcohol from said distillation column, introducing said side stream into a stripping column and separating a second methanol fraction overhead and a tertiary alcohol bottoms fraction from said side stream, and recycling said methanol overhead fraction from the stripping column to the upper part of the distillation column and recycling the overhead methanol fraction from the distillation column to the feed stream to said reactor.

2. A method according to claim 1 in which said side stream comprises from about 30 to 50 percent of said tertiary alcohol.

3. A method according to claim 1 in which said side stream comprises about 40 percent tertiary alcohol.

4. A method according to claim 1 in which said stripping column is about one-tenth the capacity of said first distillation column.

5. A method according to claim 1 in which said side stream withdrawn from said distillation column is withdrawn from an intermediate zone of said distillation column above the feed inlet to said distillation column.

6. A method according to claim 1 in which said methanol overhead fraction from the distillation column is essentially free of tertiary alcohol.

7. A method according to claim 1 in which said tertiary alcohol bottoms fraction is blended with said ether fraction.

8. In a method for the production of methyl tertiary butyl ether from the reaction of methanol and an isobutylene hydrocarbon feed stream in a catalytic reactor wherein water is added to the reaction product from said reaction resulting in the formation of an organic hydrocarbon phase comprising methyl tertiary butyl ether and unreacted hydrocarbons and an aqueous phase comprising methanol and tertiary butanol and wherein said organic hydrocarbon phase is separated to recover a methyl tertiary butyl ether fraction and said aqueous phase is distilled in a first distillation column to separate a methanol fraction overhead, the improvement which comprises withdrawing a side stream rich in tertiary butanol from said distillation column, introducing said side stream into a stripping column and separating a second methanol fraction overhead and a tertiary butanol bottoms fraction from said side stream and recycling said methanol overhead fraction from the stripping column to the upper part of the distillation column and recycling the overhead methanol fraction from the distillation column to the feed stream to said reactor.

9. A method according to claim 8 in which said side stream comprises about 40 percent of said tertiary butanol.

10. A method according to claim 8 in which said tertiary butanol fraction and said methyl tertiary butyl ether fraction are blended.

11. In a two-step method for the production of an ether from the reaction of methanol and an isoolefin hydrocarbon feed stream in which the hydrocarbons have from 4 to 7 carbon atoms in a first and a second catalytic reactor having a distillation stage between said reactors wherein the bottom product from said distillation stage is combined with the reaction product from said second catalytic reactor and wherein water is added to said mixture resulting in the formation of an organic hydrocarbon phase comprising said ether and unreacted hydrocarbons and an aqueous phase comprising methanol and a tertiary alcohol, and wherein from said organic hydrocarbon phase is separated an ether fraction and said aqueous phase is separated in a distillation column to separate a methanol fraction overhead from said aqueous phase, the improvement which comprises withdrawing a side stream rich in tertiary alcohol from said water separation distillation column, introducing said side stream into a stripping column and separating a second methanol fraction overhead and a tertiary alcohol bottoms fraction from said side stream, and recycling said methanol overhead fraction from the stripping column to the upper part of the distillation column and recycling the overhead methanol fraction from the distillation column to the feed stream to said first reactor.

* * * * *